(12) United States Patent
Curran et al.

(10) Patent No.: US 11,052,208 B2
(45) Date of Patent: Jul. 6, 2021

(54) EXHAUST VALVE SHROUD FOR A PERSONAL PROTECTION RESPIRATORY DEVICE

(71) Applicant: 3M INNOVATIVE PROPERTIES COMPANY, St. Paul, MN (US)

(72) Inventors: Desmond T. Curran, Duham (GB); Sabeel Ullah, High Wycombe (GB); Benjamin H. Cooper, Bishop Auckland (GB)

(73) Assignee: 3M Innovative Properties Company, St. Paul, MN (US)

( * ) Notice: Subject to any disclaimer, the term of this patent is extended or adjusted under 35 U.S.C. 154(b) by 306 days.

(21) Appl. No.: 16/301,867

(22) PCT Filed: May 17, 2017

(86) PCT No.: PCT/US2017/033014
§ 371 (c)(1),
(2) Date: Nov. 15, 2018

(87) PCT Pub. No.: WO2017/205127
PCT Pub. Date: Nov. 30, 2017

(65) Prior Publication Data
US 2019/0151591 A1 May 23, 2019

(30) Foreign Application Priority Data
May 25, 2016 (GB) ...................... 1609168

(51) Int. Cl.
*A61M 16/06* (2006.01)
*A62B 18/10* (2006.01)
(Continued)

(52) U.S. Cl.
CPC .......... *A61M 16/06* (2013.01); *A61M 16/107* (2014.02); *A61M 16/208* (2013.01);
(Continued)

(58) Field of Classification Search
CPC ....... A62B 18/00; A62B 18/02; A62B 18/025; A62B 18/08; A62B 18/10; A62B 9/02;
(Continued)

(56) References Cited

U.S. PATENT DOCUMENTS 3,459,216 A 8/1969 Bloom
3,643,686 A 2/1972 Koegel
(Continued)

FOREIGN PATENT DOCUMENTS

CN 2414413 11/2005
CN 2505484 3/2014
(Continued)

OTHER PUBLICATIONS

International Search Report for PCT International Application No. PCT/US2017/033014, dated May 17, 2017, 5 pages.

*Primary Examiner* — Joseph D. Boecker
(74) *Attorney, Agent, or Firm* — Steven A. Bern; Dena M. Ehrich

(57) ABSTRACT

An exhaust valve shroud for a personal protection respiratory device, the shroud comprising a main body defining an inlet for receiving exhaled air from an exhalation valve, an outlet for emitting exhaled air from the shroud, and a perimeter flow conduit for carrying the exhaled air from the inlet to the outlet, wherein the perimeter flow conduit includes a bifurcated transition section which receives air from the inlet in a substantially forward facing direction and directs the air into first and second substantially downwardly extending flow passages, each of which passages are in communication with the outlet.

12 Claims, 3 Drawing Sheets

(51) Int. Cl.
*A61M 16/20* (2006.01)
*A62B 23/02* (2006.01)
*F16K 15/14* (2006.01)
*A61M 16/10* (2006.01)

(52) U.S. Cl.
CPC ............ *A62B 18/10* (2013.01); *A62B 23/025* (2013.01); *F16K 15/148* (2013.01)

(58) Field of Classification Search
CPC ......... A62B 7/10; A62B 23/02; F16K 15/148; A61M 16/06; A61M 16/208; A41D 13/11
See application file for complete search history.

(56) References Cited

U.S. PATENT DOCUMENTS

| | | | |
|---|---|---|---|
| 3,794,036 A | 2/1974 | Carroll | |
| 3,863,630 A | 2/1975 | Cavallo | |
| 4,098,296 A | 7/1978 | Grasso | |
| 4,253,455 A | 3/1981 | Netteland | |
| 4,266,539 A | 5/1981 | Parker | |
| 4,606,340 A | 8/1986 | Ansite | |
| 4,705,068 A | 11/1987 | Hartshorn | |
| 4,850,346 A | 7/1989 | Michel | |
| D303,586 S | 9/1989 | Rudolph | |
| D305,165 S | 12/1989 | Rudolph | |
| 4,915,128 A | 4/1990 | Masserini | |
| 4,934,362 A | 6/1990 | Braun | |
| 4,958,661 A | 9/1990 | Holtermann | |
| 5,036,843 A | 8/1991 | Schreurs | |
| 5,044,395 A | 9/1991 | Vadasz F | |
| 5,086,768 A | 2/1992 | Niemeyer | |
| 5,598,872 A | 2/1997 | Kasugai | |
| 5,672,053 A | 9/1997 | Sabha | |
| 5,885,064 A | 3/1999 | McCoy | |
| 5,918,628 A | 7/1999 | Harding | |
| 6,557,549 B2 | 5/2003 | Schmidt | |
| 6,629,531 B2 | 10/2003 | Gleason | |
| 6,668,830 B1 | 12/2003 | Hansen | |
| 6,736,137 B1 * | 5/2004 | Resnick | A62B 18/10 128/201.25 |
| 7,013,895 B2 | 3/2006 | Martin | |
| 7,066,177 B2 | 6/2006 | Pittaway | |
| 7,428,903 B1 | 9/2008 | Japuntich | |
| 7,475,864 B2 | 1/2009 | Tanaka | |
| 7,673,653 B2 | 3/2010 | Mijers | |
| 8,360,104 B2 | 1/2013 | Shereyk | |
| 8,365,771 B2 | 2/2013 | Xue | |
| 8,381,764 B2 | 2/2013 | Matsubara | |
| 8,602,062 B2 | 12/2013 | Eiermann | |
| 8,622,089 B2 | 1/2014 | Tanaka | |
| 8,627,852 B2 | 1/2014 | Hatton | |
| 8,668,168 B1 | 3/2014 | Kelley | |
| 8,910,663 B2 | 12/2014 | Kern | |
| 2009/0133700 A1 * | 5/2009 | Martin | A62B 18/10 128/207.12 |
| 2011/0036347 A1 * | 2/2011 | Morgan, III | A62B 18/025 128/201.19 |
| 2011/0036408 A1 | 2/2011 | Desai | |
| 2011/0139158 A1 * | 6/2011 | Xue | A62B 18/10 128/206.15 |
| 2012/0168658 A1 | 7/2012 | Insley | |
| 2014/0076325 A1 | 3/2014 | Rosert | |
| 2014/0345607 A1 | 11/2014 | Skov | |
| 2015/0000748 A1 | 1/2015 | Shelcoviz | |
| 2015/0136141 A1 | 5/2015 | Mittelstadt | |
| 2015/0151143 A1 | 6/2015 | Langford | |
| 2015/0290478 A1 | 10/2015 | Curran | |

FOREIGN PATENT DOCUMENTS

| | | | |
|---|---|---|---|
| CN | 103656902 | 3/2014 | |
| CN | 203989554 | 12/2014 | |
| CN | 104784842 | 7/2015 | |
| CN | 205215979 | 5/2016 | |
| WO | WO 2014-035641 | 3/2014 | |
| WO | WO-2014081788 A2 * | 5/2014 | ........... A62B 18/006 |
| WO | WO 2015-009679 | 1/2015 | |

* cited by examiner

FIG. 3

EXHAUST VALVE SHROUD FOR A PERSONAL PROTECTION RESPIRATORY DEVICE

CROSS REFERENCE TO RELATED APPLICATIONS

This application is a national stage filing under 35 U.S.C. 371 of PCT/US2017/205127, filed May 17, 2017, which claims the benefit of Great Britain Application No. 1609168.8 filed May 25, 2016, the disclosure of which is incorporated by reference in its/their entirety herein.

TECHNICAL FIELD OF THE INVENTION

The present invention relates to an exhaust apparatus for personal protection respiratory devices, particularly, but not exclusively to negative pressure respirators. In particular, the present invention relates to a shroud for a respirator exhalation valve.

BACKGROUND

Negative pressure respirators are well known in the art. With respirators of this type, filtered air is drawn into the enclosed space between the inside of the respirator and a wearer's face through a filter system by the wearer's breathing action. When the wearer draws a breath, negative pressure is created in the respirator and air is drawn in through the filter system. When the wearer exhales a breath, spent air leaves the respirator through an exhalation valve and/or back through the filter system.

Although negative pressure respirators are available in many different configurations, many such respirators have an exhalation valve which closes during inhalation to ensure the inhaled air passes through the filter system and opens during exhalation to expel spent air to atmosphere. It is known to provide a diaphragm valve in which the diaphragm sits on a seat forming a seal when the valve is closed and lifts off the seat to open under the action of the exhaled breath.

The exhalation valve typically has a shroud positioned on the exterior of the valve which protects the valve from the exterior environment. The shroud is intended to serve two principal functions. Firstly, it protects the valve from suffering damage, for example, by physical impact. Secondly, it prevents, or at least reduces, the deposition of airborne particulate matter, such as paint particles, onto the diaphragm. The shroud is often removable from the valve so that it may be replaced in service in the event of damage or excessive particulate deposition.

It will be appreciated that the term "negative pressure" refers to the negative pressure generated in the respirator as the user breaths in through the filter system. Conversely, during the exhale breath, the pressure in the respirator is positive, that is to say, above atmospheric pressure as air is driven through the exhalation valve and shroud to atmosphere. The extent of this positive pressure is dependent on three factors, the pressure drop across the valve, the pressure drop across the shroud, and the respiratory effort of the user.

Accordingly, a recognized problem with the exhalation valve and shroud is that the valve and shroud generate resistance against the exhale breath due to the pressure drop observed thereacross. This resistance and resultant pressure drop is generated by a combination of: i) the restricted cross section of the air passage through the valve relative to breathing straight out to atmosphere, ii) the work required to open the valve and maintain the valve in the open position through the exhale breath, and iii) the frictional losses generated by the flow of the exhaled air through the shroud.

It is also recognized that the valve and shroud should not impinge on the line of sight of the user. Respirators are typically worn in environments in which the user is performing a skilled operation such as paint spraying. As a result, an important design consideration is that the respirator presents as little impediment to the user's activity as possible.

A further problem with prior art shrouds is that there is a tendency for airborne particles to fall under the action of gravity onto the shroud outlet and potentially deposit on the valve diaphragm.

It is an object of the invention to reduce the pressure drop across the shroud and thereby reduce the respiratory effort required to exhale air from the respirator. A further object is to provide a shroud which does not present a significant impediment to the existing line of sight of the user. Another object is to provide a shroud which limits the potential for airborne particles to deposit on the valve diaphragm.

Accordingly, an aspect of the present invention provides an exhaust valve shroud for a personal protection respiratory device, the shroud comprising a main body defining:

an inlet for receiving exhaled air from an exhalation valve, an outlet for emitting exhaled air from the shroud, and a perimeter flow conduit for carrying the exhaled air from the inlet to the outlet, wherein the perimeter flow conduit includes a bifurcated transition section which receives air from the inlet in a substantially forward facing direction and directs the air into first and second substantially downwardly extending flow passages, each of which passages are in communication with the outlet.

The provision of a bifurcated transition portion in communication with downwardly extending flow passages reduces the pressure drop over prior art devices whilst also reducing the risk of particulate deposition onto the diaphragm. A particular advantage is that the bifurcation of the flow path permits the flow path to deliver an increase in cross-sectional area as the spent air flows through the shroud.

This is in contrast to prior art shrouds which typically have a forward facing linear flow from inlet to outlet. Frequently, prior art shrouds have a forward facing air flow which exits the valve and hits a protective baffle. This arrangement presents a significant and abrupt pressure drop to atmosphere which must be overcome by the user of the respirator in the exhale breath if flow rate is not to be impaired. This increases the respiratory effort of the user for any given physiological respiratory load. Furthermore the forward facing outlet can be susceptible to permitting particulate deposition onto the valve diaphragm.

Thus, the shroud of the present invention is able to deliver a reduced pressure drop across the valve for any given flow rate. This presents a significant benefit to the user in that the respiratory effort of the user for any given physiological respiratory load is reduced over the prior art shrouds. The shroud of the present invention also reduces the extent of particulate deposition onto the valve diaphragm.

Preferably, the first and second substantially downwardly extending flow passages are positioned on first and second sides, respectively, of the inlet.

Advantageously by directing the spent air into two flow passages arranged either side of the inlet the increased cross-sectional area of flow is achieved without impairing the line of sight of the user.

Preferably, the bifurcated transition portion defines a flow chamber having curved sidewalls which transition the forward flow from the inlet into the substantially downwardly extending flow passages.

Advantageously, the curved sidewalls present a low resistance flow path for the exhaled air which reduces the pressure drop across the shroud. The provision of the chamber allows for a relatively gradual transition of the flow direction which reduces frictional losses thereby reducing pressure drop.

Preferably, the inlet comprises an upper inlet in communication with the perimeter flow conduit and a lower inlet in communication with the outlet via a substantially forwardly extending central flow conduit.

Preferably, the lower inlet is positioned, in use, below the upper inlet.

Preferably, the outlet is positioned, in use, below the upper inlet.

Advantageously, this feature allows the outlet to be positioned, at least in part, in a downward facing direction. This reduces the risk of particulate deposition on the diaphragm.

Preferably, the first and second substantially downwardly extending flow passages pass at least part of first and second sides, respectively, of the lower inlet.

Preferably, the main body includes a front section which defines the outlet.

Preferably, the front section defines first and second perimeter portions of the outlet which are associated with the first and second substantially downwardly extending flow passages, respectively.

Preferably, the front section defines a central portion of the outlet which is associated with the central flow conduit.

Preferably, the central portion of the outlet defines louvres which are positioned to be substantially aligned with the flow in the substantially forwardly extending central flow conduit.

Preferably, the main body defines a rear section which forms an airtight connection to the exhaust valve.

Preferably, the airtight connection comprises a releasable push fit connection or a permanent attachment.

BRIEF DESCRIPTION OF THE DRAWINGS

The present invention will now be described by way of example only, and with reference to the accompanying drawings, in which:

FIG. 3 is an exploded rear perspective view of the shroud of FIG. 1 and the exhalation valve of the negative pressure respirator.

DETAILED DESCRIPTION OF THE PREFERRED EMBODIMENTS

Figure 1:
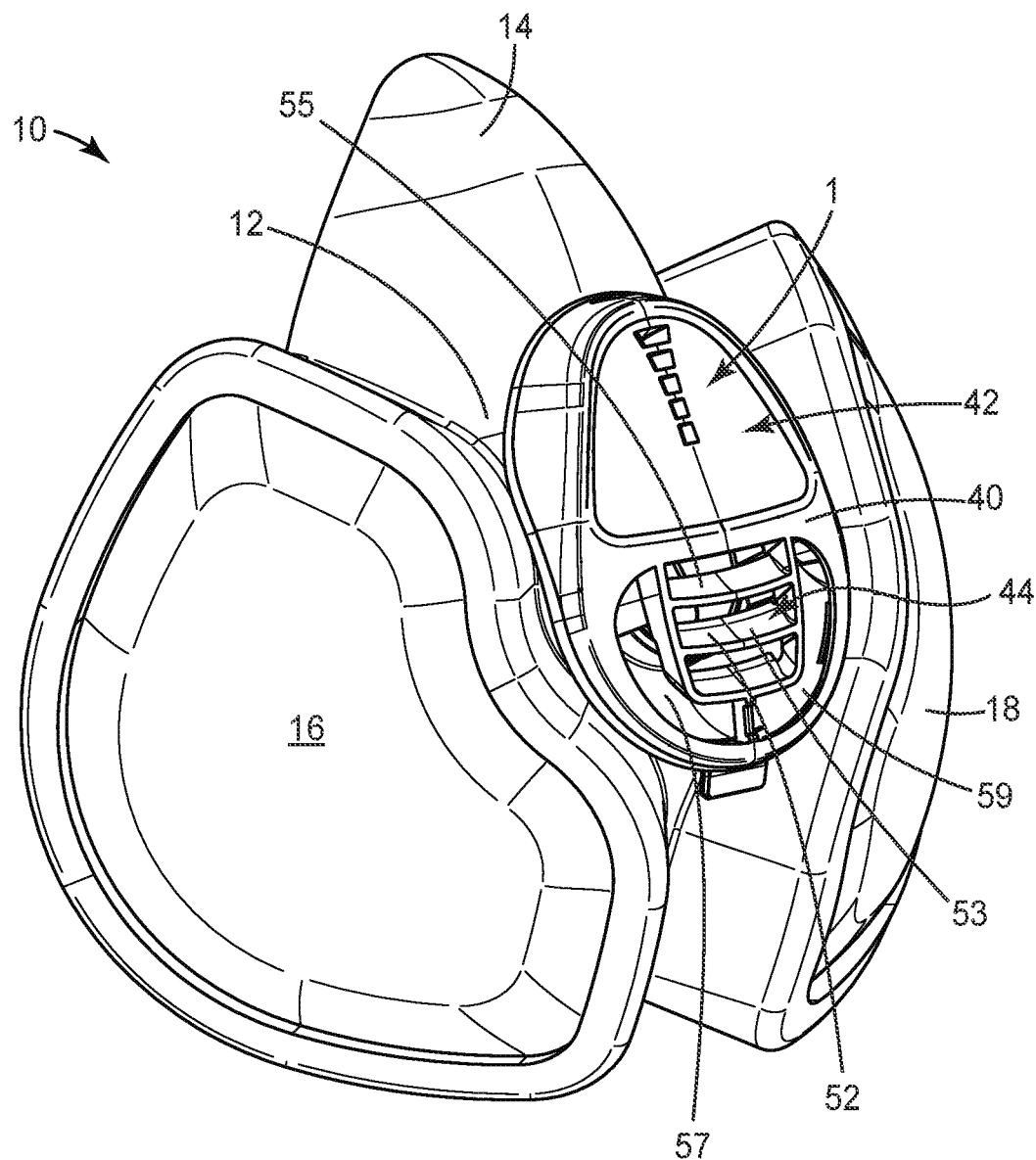
FIG. 1 is front side perspective view of the shroud of the present invention affixed to a negative pressure respirator.

FIG. 1 shows an exhalation valve shroud 1, referred to herein as shroud 1, attached to a negative pressure respirator 10, referred to herein as respirator 10. By way of example only the respirator 10 is a 3M® 4000 Series respirator.

The respirator 10 has a face mask 12 which forms a substantially airtight seal with the face of the user. The face mask includes a nose section 14 which covers the nose of the user to allow the respirator 10 to provide effective filtration of air breathed in through the nose or the mouth. Air enters the respirator 10 through first and second filters 16, 18, respectively. The respirator 10 is held in position on the face of the user by compliant straps which are not shown for clarity. The respirator has an exhalation valve 20 (not shown in FIG. 1) which is positioned at the front of the mask 12 at a position approximately in line with the mouth of the user. The exhalation valve 20 closes on inhalation to ensure that the inhaled air passes through the filters 16, 18, and opens on exhalation to emit the exhaled air from the mask 12.

Figure 2:
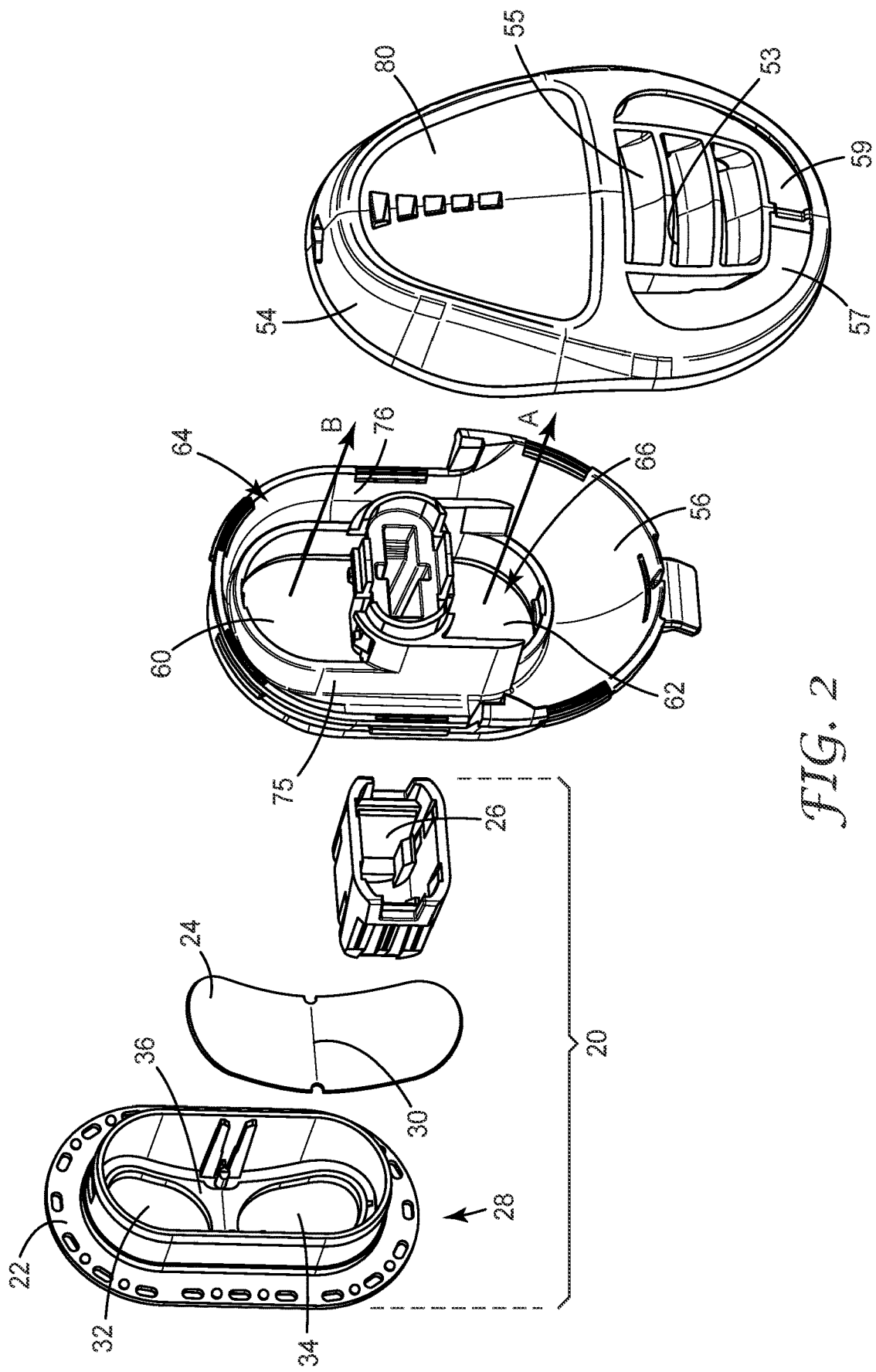
FIG. 2 is an exploded front perspective view of the shroud of FIG. 1 and the exhalation valve of the negative pressure respirator.
Figure 3:
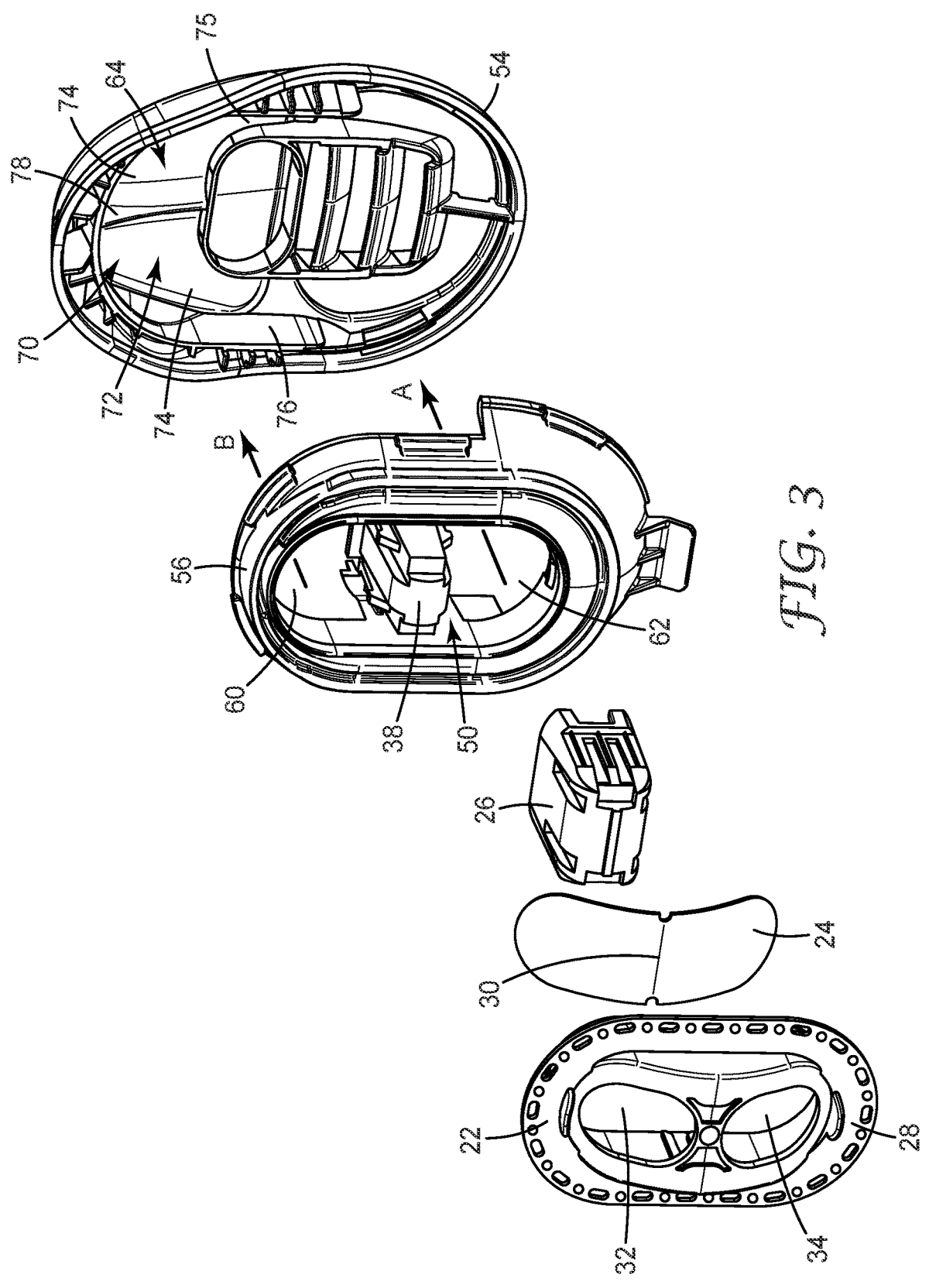

Turning to FIGS. 2 and 3, the valve 20 is shown in exploded view having a valve chassis 22, a valve diaphragm 24 and a socket 26. The rear face 28 of the chassis 22 is attached to the face mask 12 of the respirator 10. The diaphragm 24 has a central axis 30 which forms the point of attachment of the diaphragm 24 to the chassis 22. The socket 26 abuts the diaphragm 24 to the chassis 22 and is fixedly attached to the chassis 22. In use, the diaphragm 24 deflects under the action of the exhaled breath allowing air to pass in a forward direction through upper and lower ports 32, 34 in the chassis 22. During inhalation the diaphragm 24 is urged onto a valve seat 36 provided by the chassis 22.

The shroud 1 is attached to exhalation valve 20 at the front of the mask 10 so that all the exhaled air passes through the shroud 1. The shroud 1 is attached to the socket by way of a plug 38 (see FIG. 3) which engages with the socket 26 to provide either permanent or releasable attachment of the shroud 1 to the respirator 10.

Returning briefly to FIG. 1, the shroud is shown having a main body 40 which has an upper portion indicated generally at 42 and a lower portion indicated generally at 44. The main body defines an inlet 50 (not shown in FIG. 1) and an outlet 52. The outlet has a central portion 53 which has a series of louvres 55 and first and second perimeter portions 57, 59 as will be described in further detail shortly.

In FIGS. 2 and 3 the shroud 1 is shown having a front section 54 and a rear section 56. The rear section 56 is attached to the plug 38. The front section 54 and a rear section 56 collectively define the internal flow passages of the shroud between the inlet indicated generally at 50 in FIG. 3 and the outlet 52. The outlet 52 has a central portion 53 and first and second perimeter portions 57, 59 as will be described in further detail shortly.

Exhaled air enters the shroud 1 from the exhale valve 20 via the inlet 50 which is defined by an upper inlet 60 and a lower inlet 62. Air entering via the lower inlet 62 enters a central flow conduit indicated generally at 66. The perimeter flow conduit 64 and the central flow conduit 66 are both in fluid communication with the outlet 52. The perimeter flow conduit 64 is principally associated with the first and second perimeter portions 57, 59 of the outlet 52 and the central flow conduit 66 is principally associated with the central portion 53 of the outlet 52. However, it will be noted that a limited proportion of the flow through the central conduit 66 may exit through the first and second perimeter portions 57, 59 and likewise a limited proportion of the flow through the perimeter flow conduit 64 may exit through the central portion 53.

Flow through the central conduit 66 moves in a substantially forward facing direction A from the lower port 34 in the chassis 22, through the conduit 66 and out to atmosphere through the central portion 53 of the outlet 52.

Flow through the perimeter flow conduit 64 enters the shroud through the upper port 32 in the chassis 22 in a substantially forward facing direction B and enters a bifurcated transition portion 70 (see FIG. 3). The bifurcated transition portion 70 forms a flow chamber 72 having curved sidewalls 74 which transition the forward flow from the upper inlet 60 into the substantially downwardly extending first and second flow passages 75, 76. This transition is assisted by a splitter 78 on an inner surface of a front wall 80 of the main body 40. The splitter 78 directs the air flow from the upper inlet 60 onto the curved sidewalls 74 and thereby promotes the smooth bifurcation of the flow from the upper inlet 60 into the first and second flow passages 74, 76.

This smooth transition from a unitary air flow into a bifurcated airflow reduces pressure drop in the shroud 1 by limiting frictional losses associated with transition in air flow direction and also provides an increased cross-sectional flow area.

The provision of a flow chamber 72 provides the space in which to execute this change in flow direction in the most efficient manner so as to minimize pressure drop without significantly impeding on the line of sight of the user.

Once the flow has transitioned from the forward facing direction B into the substantially downwardly extending first and second flow passages 74, 76 it passes either side of the upper inlet 60 and then passes either side of the lower inlet 62 and then on to the first and second perimeter portions 57, 59 of the outlet 52.

Accordingly the outlet 52 is positioned below the upper inlet 60 and the upper portion 42 of the main body 40 protects the internal flow paths and the diaphragm from the deposition of airborne particulates. This configuration therefore presents significant benefits in the extent of protection offered against the deposition of airborne particulates compared with prior art devices.

It will be appreciated that the terms forward, down, and all other relational descriptions used herein are referenced to the position of the shroud when the respirator is in its in use configuration on the face of a user.

The invention claimed is:

1. An exhaust valve shroud for a personal protection respiratory device, the shroud comprising a main body defining:
    an inlet for receiving exhaled air from an exhalation valve,
    an outlet for emitting exhaled air from the shroud, and
    a perimeter flow conduit for carrying the exhaled air from the inlet to the outlet,
    wherein the perimeter flow conduit includes a bifurcated transition section which receives exhaled air from the inlet in a substantially forward facing direction and directs the exhaled air into first and second substantially downwardly extending flow passages, each of which passages are in communication with the outlet;
    wherein the inlet comprises an upper inlet in communication with the perimeter flow conduit and a lower inlet in communication with the outlet via a substantially forwardly extending central flow conduit.

2. The exhaust valve shroud as claimed in claim 1, wherein the first and second substantially downwardly extending flow passages are positioned on first and second sides, respectively, of the inlet.

3. The exhaust valve shroud as claimed in claim 2 wherein the bifurcated transition portion defines a flow chamber having curved sidewalls which transitions the forward flow from the inlet into the substantially downwardly extending flow passages.

4. The exhaust valve shroud as claimed in claim 1 wherein the lower inlet is positioned, in use, below the upper inlet.

5. The exhaust valve shroud as claimed in claim 1, wherein the outlet is positioned, in use, below the upper inlet.

6. The exhaust valve shroud as claim 1 wherein the first and second substantially downwardly extending flow passages pass at least part of first and second sides, respectively, of the lower inlet.

7. The exhaust valve shroud as claimed in claim 6 wherein the main body includes a front section which defines the outlet.

8. The exhaust valve shroud as claimed in claim 7 wherein the front section defines first and second perimeter portions of the outlet which are associated with the first and second substantially downwardly extending flow passages, respectively.

9. The exhaust valve shroud as claimed in claim 6 wherein the front section defines a central portion of the outlet which is associated with the central flow conduit.

10. The exhaust valve shroud as claimed in claim 9 wherein the central portion of the outlet defines louvres which are positioned to be substantially aligned with the central flow conduit.

11. The exhaust valve shroud as claimed claim 1, wherein the main body defines a rear section which forms an airtight connection to the exhalation valve.

12. The exhaust valve shroud as claimed in claim 11 wherein the airtight connection comprises a releasable push fit connection or a permanent attachment.

* * * * *

UNITED STATES PATENT AND TRADEMARK OFFICE
CERTIFICATE OF CORRECTION

| | | |
|---|---|---|
| PATENT NO. | : 11,052,208 B2 | Page 1 of 1 |
| APPLICATION NO. | : 16/301867 | |
| DATED | : July 6, 2021 | |
| INVENTOR(S) | : Curran et al. | |

It is certified that error appears in the above-identified patent and that said Letters Patent is hereby corrected as shown below:

In the Specification

Column 1, Line 9, Delete "PCT/US2017/205127," and insert -- PCT/US2017/033014, --, therefor.

In the Claims

Column 6, Line 22 (Approx.), In Claim 6, after "as" insert -- claimed in --.

Column 6, Line 41 (Approx.), In Claim 11, after "claimed" insert -- in --.

Signed and Sealed this
Nineteenth Day of April, 2022

*Katherine Kelly Vidal*

Katherine Kelly Vidal
*Director of the United States Patent and Trademark Office*